United States Patent
Romano et al.

(10) Patent No.: US 11,872,344 B2
(45) Date of Patent: Jan. 16, 2024

(54) DETECTING AND TREATING COPD-OSA OVERLAP SYNDROME

(71) Applicant: KONINKLIJKE PHILIPS N.V., Eindhoven (NL)

(72) Inventors: Robert Romano, Pittsburgh, PA (US); Richard James McKenzie, Jr., Butler, PA (US)

(73) Assignee: Koninklijke Philips N.V., Eindhoven (NL)

( * ) Notice: Subject to any disclaimer, the term of this patent is extended or adjusted under 35 U.S.C. 154(b) by 678 days.

(21) Appl. No.: 17/015,451

(22) Filed: Sep. 9, 2020

(65) Prior Publication Data
US 2021/0093819 A1    Apr. 1, 2021

Related U.S. Application Data

(60) Provisional application No. 62/908,093, filed on Sep. 30, 2019.

(51) Int. Cl.
*A61M 16/06* (2006.01)
*A61M 16/00* (2006.01)

(52) U.S. Cl.
CPC ........ *A61M 16/06* (2013.01); *A61M 16/0003* (2014.02); *A61M 16/024* (2017.08); *A61M 2205/50* (2013.01)

(58) Field of Classification Search
CPC ...... A61M 2205/50; A61M 2205/3337; A61M 2230/005; A61M 16/0057;
(Continued)

(56) References Cited

U.S. PATENT DOCUMENTS 9,084,859 B2    7/2015  Connor
9,220,856 B2 *  12/2015 Martin ............. A61M 16/0003
(Continued)

FOREIGN PATENT DOCUMENTS

WO    2014186584 A2    11/2014

OTHER PUBLICATIONS

International Search Report for PCT/EP2020/076875 dated Sep. 25, 2020.
(Continued)

*Primary Examiner* — Joseph D. Boecker
*Assistant Examiner* — Thomas W Greig
(74) *Attorney, Agent, or Firm* — Daniel H. Brean; Andrew M. Gabriel (57) ABSTRACT

The present ventilator system, for detecting and treating concurrent chronic obstructive pulmonary disease (COPD) and obstructive sleep apnea (OSA event(s)) overlap syndrome, comprises a pressure generator for generating a pressurized flow of breathable gas for delivery to an airway of a subject; sensor(s) for generating output signals conveying information related to breathable gas parameters; and processor(s) operatively connected to the sensor(s) and the pressure generator, configured to: detect presence of OSA event(s) and/or expiratory flow limitation (EFL) in the subject based on the output signals. Responsive to detecting concurrent presence of OSA event(s) and EFL, the processors are configured to determine OSA EVENT(S) therapy parameters for treating the detected OSA event(s) in the subject; determine EFL therapy parameters for treating the detected EFL in the subject; determine a priority treatment based on a comparison between the OSA event(s) therapy parameters and the EFL therapy parameters; and control the pressure generator.

24 Claims, 4 Drawing Sheets

(58) Field of Classification Search
CPC .......... A61M 16/0066; A61M 16/0072; A61M 2230/40; A61M 2205/3334; A61M 16/0069; A61M 2205/52; A61M 16/00–0026; A61B 5/0826; A61B 5/08; A61B 5/0816; A61B 5/4818; A61B 1/24; G01N 2800/122

See application file for complete search history.

(56) References Cited

U.S. PATENT DOCUMENTS

| | | | |
|---|---|---|---|
| 9,827,388 B2 | 11/2017 | Bassin | |
| 2002/0185130 A1* | 12/2002 | Wright | A61M 16/085 600/533 |
| 2010/0108066 A1* | 5/2010 | Martin | A61M 16/0672 128/204.23 |
| 2012/0289852 A1* | 11/2012 | Van Den Aardweg | A61B 5/085 600/533 |
| 2016/0193438 A1* | 7/2016 | White | A61M 16/026 128/204.23 |
| 2016/0361012 A1* | 12/2016 | Chen | A61B 5/7225 |
| 2020/0157090 A1 | 5/2020 | Hill | |
| 2020/0297955 A1* | 9/2020 | Shouldice | G16H 50/20 |

OTHER PUBLICATIONS

Dragonieri, S. et al., "Exhaled breath profiling in patients with COPD and OSA overlap syndrome: A pilot study". Journal in Breath Research, Oct. 2016.

Weitzenblum, E. et al., "Overlap Syndrome: Obstructive sleep apnea in patients with chronic obstructive pulmonay disease". Proceedings of the American Thoracic Society, vol. 5, pp. 237-241, 2008.

* cited by examiner

DETECTING AND TREATING COPD-OSA OVERLAP SYNDROME

CROSS-REFERENCE TO RELATED APPLICATIONS

This patent application claims the priority benefit under 35 U.S.C. § 119(e) of U.S. Provisional Application No. 62/908,093, filed on Sep. 30, 2019, the contents of which are herein incorporated by reference.

BACKGROUND

1. Field

The present disclosure pertains to a ventilator system and method for detecting and treating COPD-OSA overlap syndrome.

2. Description of the Related Art

Chronic Obstructive Pulmonary Disease (COPD) and Obstructive Sleep Apnea (OSA) event(s) (and/or inspiratory flow limited occurrences) may be separately associated with several comorbidities. The coexistence of the two conditions, referred to as COPD-OSA Overlap Syndrome, may act as a predisposing factor for a higher prevalence of comorbidities compared to those associated with each disease separately. Currently, there are no adequate medical solutions available that simultaneously addresses these two conditions. Therefore, there is a need for a single medical device that can treat a subject that suffers from COPD-OSA Overlap Syndrome.

SUMMARY

Accordingly, one or more aspects of the present disclosure relate to a ventilator system for detecting and treating concurrent chronic obstructive pulmonary disease (COPD) and obstructive sleep apnea (OSA) overlap syndrome. The system comprises a pressure generator configured to generate a pressurized flow of breathable gas for delivery to an airway of a subject. The system comprises one or more sensors configured to generate output signals conveying information related to one or more breathable gas parameters.

The system comprises one or more physical computer processors operatively connected to the one or more sensors and the pressure generator, the one or more physical computer processors configured by computer readable instructions to: detect presence of obstructive sleep apnea OSA event(s) and/or expiratory flow limitation (EFL) in the subject based on the output signals. Responsive to detecting concurrent presence of OSA event(s) and EFL, the one or more physical computer processors are configured to determine one or more OSA event(s) therapy parameters for treating the detected obstructive sleep apnea in the subject; determine one or more EFL therapy parameters for treating the detected expiratory flow limitation in the subject; determine a priority treatment based on a comparison between the one or more OSA event(s) therapy parameters and the EFL therapy parameters; and control the pressure generator to deliver the determined priority treatment to the subject.

Another aspect of the present disclosure relates to a method for detecting and treating concurrent chronic obstructive pulmonary disease (COPD) and obstructive sleep apnea (OSA) event(s) overlap syndrome with a ventilator system. the ventilator system comprises a pressure generator, one or more sensors, and one or more physical computer processors operatively connected to the one or more sensors and the pressure generator. the method comprises generating a pressurized flow of breathable gas for delivery to the airway of a subject with the pressure generator; generating output signals conveying information related to one or more parameters of the breathable gas with the one or more sensors; detecting, with the one or more physical computer processors, presence of obstructive sleep apnea OSA event(s) and/or expiratory flow limitation (EFL) in the subject based on the output signals. Responsive to detecting concurrent presence of OSA event(s) and EFL, determining, with the one or more physical computer processors, one or more OSA event(s) therapy parameters for treating the detected obstructive sleep apnea or other upper airway concerns that create flow limitation or decrease the patency of the subject's airway determining, with the one or more physical computer processors, one or more EFL therapy parameters for treating the detected expiratory flow limitation in the subject; determining, with the one or more physical computer processors, a priority treatment based on a comparison between the one or more OSA event(s) therapy parameters and the EFL therapy parameters; and controlling, with the one or more physical computer processors, the pressure generator to deliver the determined priority treatment to the subject.

Still another aspect of the present disclosure relates to a ventilator system for detecting and treating concurrent chronic obstructive pulmonary disease (COPD) and obstructive sleep apnea (OSA) overlap syndrome. The system comprises means for generating a pressurized flow of breathable gas for delivery to an airway of a subject; means for generating output signals conveying information related to one or more breathable gas parameters; means for detecting presence of obstructive sleep apnea OSA event(s) and/or expiratory flow limitation (EFL) in the subject based on the output signals; means for determining one or more OSA event(s) therapy parameters for treating the detected obstructive sleep apnea in the subject, responsive to detecting concurrent presence of OSA event(s) and EFL; means for determining one or more EFL therapy parameters for treating the detected expiratory flow limitation in the subject; means for determining a priority treatment based on a comparison between the one or more OSA event(s) therapy parameters and the EFL therapy parameters; and means for controlling the pressure generator to deliver the determined priority treatment to the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, COPD refers to occurrence of one or more conditions of chronic obstructive pulmonary disease. As used herein, OSA refers to obstructive sleep apnea event(s) and/or inspiratory flow limited occurrences.

Figure 1:
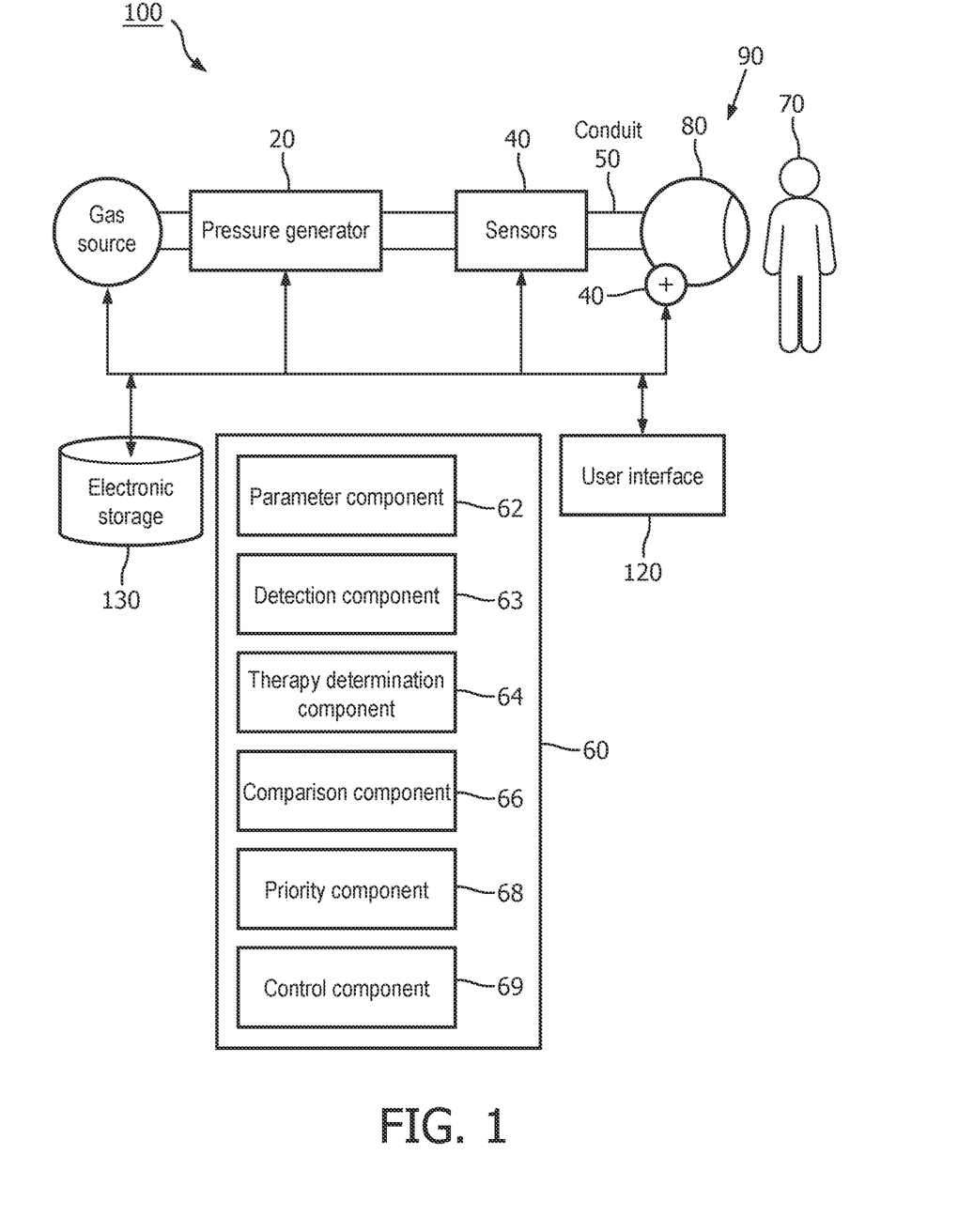
FIG. 1 illustrates an example of a ventilator system for detecting and treating COPD-OSA overlap syndrome, according to one or more embodiments.
Figure 2:
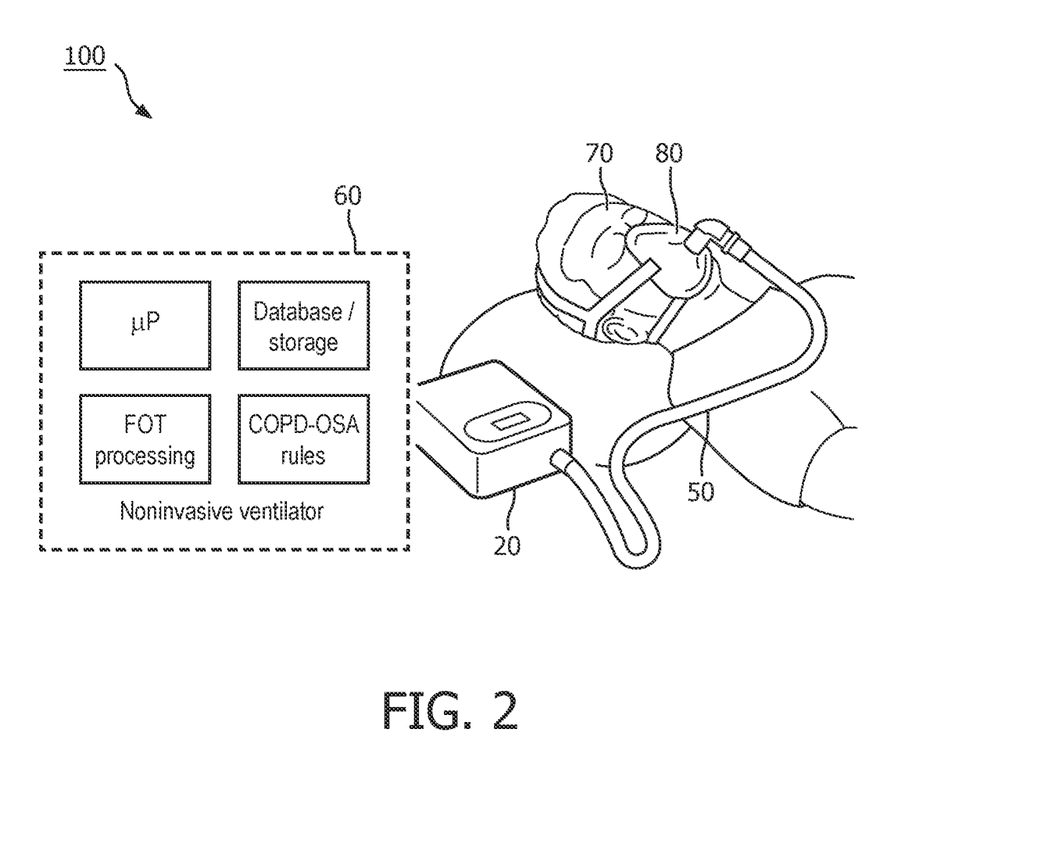
FIG. 2 illustrates an example of a ventilator system for detecting and treating COPD-OSA overlap syndrome, according to one or more embodiments.

FIGS. 1 and 2 illustrate an example of a ventilator system for detecting and treating COPD-OSA overlap syndrome in a subject 70, according to one or more embodiments. COPD and OSA event(s) are two of the most prevalent pulmonary diseases. Unfortunately, and insidiously they can occur simultaneously in a phenomenon commonly referred to as COPD-OSA Overlap Syndrome, creating twice-fold the unpleasant conditions of disordered breathing. As used herein, COPD-OSA overlap syndrome refers to concurrent obstructive sleep apnea event(s) and/or upper airway obstruction occurrences (that creates inspiratory flow limitation or decrease the patency of the subject's airway) with one or more conditions of chronic obstructive pulmonary disease. A dominant feature of COPD is a condition that affects lower airways where disease causes destruction of the parenchyma and loss of elastic recoil resulting in lower airway collapse during exhalation. This is referred to as Expiratory Flow Limitation (EFL), and is defined whenever an increase in transpulmonary pressure causes no corresponding increase in expiratory flow. OSA event(s) may be caused by partial or complete blockage of the upper airways therefore causing inspiratory flow limitation occurrence. If left untreated, the co-existence of these two pulmonary conditions further increase the possibilities of complications from cardiac disease, stroke, type two diabetes and potential increases of morbidity and mortality. Continuous Positive Airway Pressure (CPAP) therapy applied with a mask may be used to compensate for inspiratory flow limitation occurrence through increased airway collapsibility. The level of CPAP may be titrated to maintain upper airway patency and alleviate obstructive event(s). The application of an optimized level of CPAP has been demonstrated to effectively abolish a subject's Expiratory Flow Limitation, reduce their work of breathing, and treat OSA event(s) and/or upper airway obstruction occurrences. As used herein, COPD refers to occurrence of one or more conditions of chronic obstructive pulmonary disease.

Expiratory Flow Limitation (EFL), may exhibit overlapping patterns in COPD, and OSA event(s) and/or upper airway obstruction occurrences, as well as, Obesity Hypoventilation Syndrome (OHS). System 100 may be configured to titrate the ventilator's pressure by determining a preference of the airway pressure delivered to a subject. In some embodiments, the pressure required to treat a subject's upper airway obstruction may be prioritized over the pressure required to treat a subject's expiratory flow limitation.

In some embodiments, system 100 comprises one or more of a pressure generator 20, one or more sensors 40, a subject interface 90, one or more physical computer processors 60, a user interface 120, electronic storage 130, and/or other components.

In some embodiments, pressure generator 20 may include any device, such as, for example, a pump, blower, piston, or bellows, that is capable of elevating the pressure of the received gas for delivery to a subject. In some embodiments, pressure generator 20 may include one or more devices, such as for example, a valve and/or a series of valves, capable of controlling the pressure, flow rate, flow direction, and/or other parameters of the flow of gas. The present disclosure contemplates controlling the operating speed of the blower, for example, either alone or in combination with one or more valves and/or other devices contained in and/or external to pressure generator 20, to control the pressure and/or flow of gas provided to subject 70. In some embodiments, pressure generator 20 receives a flow of gas from a gas source, such as the ambient atmosphere, and elevates the pressure of that gas for delivery to the airway of subject 70. The present disclosure contemplates that gas other than ambient atmospheric air may be introduced into system 100 for delivery to the subject.

In some embodiments, pressure generator 20 is configured to generate a pressurized flow of gas for delivery to the airway of a subject 70. Pressure generator 20 may control one or more parameters of the flow of gas (e.g., flow rate, pressure, volume, temperature, gas composition, etc.) for therapeutic purposes, and/or for other purposes. By way of a non-limiting example, pressure generator 20 may be configured to control the flow rate and/or pressure of the flow of gas to provide pressure support to the airway of subject 70.

Sensor(s) 40 may be configured to generate output signals conveying information related to one or more parameters of the gas within system 100. The one or more parameters of the gas within system 100 may comprise gas parameters related to the pressurized flow of breathable gas, breathing parameters related to respiration of subject 70, physiological parameters of subject 70, and/or other parameters. The one or more gas parameters of the pressurized flow of breathable gas may comprise, for example, one or more of a flow rate, a volume, a pressure, humidity, temperature, acceleration, velocity, and/or other gas parameters. Breathing parameters related to the respiration of subject 70 may comprise a tidal volume, a timing (e.g., beginning and/or end of inhalation, beginning and/or end of exhalation, etc.), a respiration rate, a duration (e.g., of inhalation, of exhalation, of a breathing cycle, etc.), respiration frequency, and/or other breathing parameters. Physiological parameters may include oximetry parameters, pulse, heart rate, temperature, blood pressure, and/or other physiological parameters.

Sensor(s) 40 may comprise one or more sensors that measure such parameters directly (e.g., through fluid communication with the flow of gas in subject interface 90). Sensor(s) 40 may comprise one or more sensors that generate output signals related to the one or more parameters indirectly. For example, sensor(s) 40 may comprise one or more sensors configured to generate an output based on an operating parameter of pressure generator 20 (e.g., subject flow and/or pressure estimations from motor current, voltage, rotational velocity, and/or other operating parameters), and/or other sensors. In some embodiments, sensor(s) 40 may include one or more of flow, position, volume, pressure, humidity, temperature, motion, acceleration, oximetry, audio, video, photo sensors, and/or other sensors. Sensor(s) 40 may comprise sensors disposed in a plurality of locations, such as for example, at various locations within (or in communication with) a conduit 50, within pressure generator 20, within (or in communication with) subject interface 90, on subject 70, and/or other locations.

Subject interface 90 is configured to communicate the pressurized flow of breathable gas to the airway of subject 70. As such, in some embodiments, subject interface 90 comprises conduit 50, interface appliance 80, and/or other components. In some embodiments, conduit 50 is configured to convey the pressurized flow of gas to interface appliance 80. Interface appliance 80 is configured to deliver the flow of gas to the airway of subject 70. In some embodiments, interface appliance 80 is configured to be non-invasively engaged by subject 70. Non-invasive engagement comprises removably engaging one or more external orifices of the airway of subject 70 (e.g., nostrils and/or mouth) to communicate gas between the airway of subject 70 and interface appliance 80. In some embodiments, interface appliance 80 is removably coupled to conduit 50. Interface appliance 80 may be removed for cleaning and/or for other purposes. In some embodiments, conduit 50 is configured as a mouthpiece to be engaged by the mouth of subject 70.

In some embodiments, other interface appliances may be configured as interface appliance 80. Some examples of interface appliance 80 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance. For example, an endotracheal tube, a tracheotomy tube, a laryngeal mask airway, and/or other invasive interface appliances.

Processor(s) 60 is configured to provide information processing capabilities in system 100. As such, processor(s) 60 may include one or more digital processors, one or more analog processor, one or more digital circuits designed to process information, one or more analog circuits designed to process information, a state machine, and/or other mechanisms for electronically processing information. In some embodiments, processor(s) is operatively connected to sensors (40) and/or pressure generator (20). Although processor(s) 60 is shown in FIG. 1 as a single entity, this is for illustrative purposes only. In some implementations, processor(s) 60 includes a plurality of processing units. These processing units may be physically located within the same device (e.g., pressure generator 20), or processor(s) 60 may represent processing functionality of a plurality of devices operating in coordination.

As shown in FIG. 1, processor(s) 60 is configured to execute one or more computer program components. The one or more computer program components may comprise one or more of a parameter component 62, a detection component 63, a therapy determination component 64, a comparison component 66, a priority determination component 68, a control component 69, and/or other components. Processor(s) 60 may be configured to execute components 62, 63, 64, 66, 68 and 69 by software; hardware; firmware; some combination of software, hardware, and/or firmware; and/or other mechanisms for configuring processing capabilities on Processor(s) 60.

It should be appreciated that although components 62, 63, 64, 66, 68 and 69 are illustrated in FIG. 1 as being co-located within a single processing unit, in implementations in which Processor(s) 60 comprises multiple processing units, one or more of components 62, 63, 64, 66, 68 and 69 may be located remotely from the other components. The description of the functionality provided by the different components 62, 63, 64, 66, 68 and 69 described below is for illustrative purposes, and is not intended to be limiting, as any of components 62, 63, 64, 66, 68 and 69 may provide more or less functionality than is described. For example, one or more of components 62, 63, 64, 66, 68 and 69 may be eliminated, and some or all of its functionality may be provided by other components 62, 63, 64, 66, 68 and/or 69. As another example, Processor(s) 60 may be configured to execute one or more additional components that may perform some or all of the functionality attributed below to one of components 62, 64, 66, 68 and/or 69.

Parameter component 62 may be configured to receive, determine and/or obtain one or more parameters within system 100. For example, the one or more parameters may be determined based on the output signals from sensor(s) 40. In some embodiments, parameter component 62 is configured to determine one or more parameters of the gas within system 100, (e.g., parameters related to the pressurized flow of breathable gas), one or more breathing parameters related to respiration of subject 70, one or more physiological parameters of subject 70, and/or other parameters. The one or more gas parameters of the pressurized flow of breathable gas may comprise, for example, one or more of a flow rate, a volume, a pressure, humidity, temperature, acceleration, velocity, and/or other gas parameters. Breathing parameters related to the respiration of subject 70 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, AHI index (apnea and hypopnea index=number of Apnea and Hypopnea counted per sleep session divided by the number of hours per sleep session), and/or other breathing parameters. Physiological parameters may include oximetry parameters, a pulse, a heart rate, a temperature, a blood pressure, movement, and/or other physiological parameters.

Detection component 63 may be configured to detect presence of one or more respiratory conditions in the subject. Detection component 63, in some embodiments, may be configured to detect one or more respiratory conditions based on the information received from parameter component 62, or from one or more components of system 100. In some embodiments, detection component 63 may be configured to detect one or more respiratory disorders, and receive information of presence of one or more other respiratory disorders from other components within or outside system 100. For example, from a remote database, from another medical device, or from a user (e.g., a patient, healthcare provider, a user, etc.) In some embodiments, the one or more respiratory conditions detected by detection component 63 may be concurrent, consecutive, or asynchronous.

In some embodiments, a respiratory condition may indicate a condition of the respiration of the subject. For example, the respiratory condition may indicate that the condition of the respiration of the subject is normal. For example, the one or more respiratory parameters are within normal values (e.g., values of a healthy individual). In some embodiments, the respiratory condition may indicate presence of an anomaly. For example, when one or more respiratory parameters are outside of normal values. In some embodiments, the one or more respiratory conditions, detected by detection component 63, may indicate presence of one or more respiratory disorders. For example, the one or more detected conditions may indicate upper airway obstruction, lower airway obstruction, airway restriction, inspiratory flow limitation occurrence (IFL), expiratory flow limitation (EFL), and/or other disorders.

Obstructive sleep apnea (OSA) event(s) are a condition in which a subject experiences a decrease or complete stop in airflow while asleep, despite the subject continuing to try to breathe. Snoring is the vibration of respiratory structures and the resulting sound due to obstructed air movement during breathing while sleeping. In some cases, the sound may be soft, but in most cases, it can be loud and unpleasant. Snoring during sleep may be a sign, or first alarm, of obstructive sleep apnea (OSA) event(s). These event(s) occur when the muscles relax during sleep, causing soft tissue in the back of the throat to collapse and block the upper airway. This leads to partial reductions (known as hypopneas) and complete pauses (known as apneas) in breathing. An apnea event is defined as a cessation of airflow for at least 10 seconds during sleep. Hypopnea is defined as an abnormal respiratory event lasting at least 10 seconds with at least a 30 percent reduction in thoracoabdominal movement or airflow as compared to a baseline, with at least a 4 percent oxygen desaturation. Most apnea event(s) last between 10 and 30 seconds, but some may persist for one minute or longer. This can lead to abrupt reductions in blood oxygen saturation, with oxygen levels falling as much as 40 percent or more in severe cases.

In some embodiments, detection component 63 is configured to detect OSA event(s) (and/or inspiratory flow limited occurrences) based on partial or complete blockage of the upper airways of the subject. In some embodiments, OSA event(s) (and/or inspiratory flow limited occurrences) are detected based on an increase in airway inspiratory resistance due a measurable collapse of the upper airway during sleep. For example, a subject's airway collapse, or upper airway obstruction is determined by an increase in airway inspiratory resistance. In some embodiments, Forced Oscillation Technique (FOT) may be used to detect OSA event(s) (and/or inspiratory flow limited occurrences). FOT is a method (that may be delivered by ventilator system 100) for quantitatively assessing airway mechanics. In some embodiments, FOT may be well tolerated and easily applied in conjunction with a conventional ventilator sleep setup. FOT works by comparing the phase shift of the small amplitude oscillations on the flow signal to the oscillations on the pressure signal. For example, in a healthy unobstructed lung, these two signals arrive at the same time to the sensors. However, whenever there is a pulmonary obstruction or change in the inertial properties of the lung there is an offset in the arrival time between these two signals. Airway impedance can be deduced by the mechanical response to these small time varying changes. The impedance can be further broken down into two components, resistance and reactance. The resistive component is dominant in subjects who have airway restrictions such as those with upper airway obstructions. In some embodiments, the impedance measurements may be further broken down into inspiration phase and expiration phase. FOT allows analysis of the upper airway impedance and, hence, detection of obstructive sleep apnea.

Other techniques may be used to detect OSA event(s). For example, in some embodiments, detection component 63 may be configured to detect OSA event(s) based on analysis and/or monitoring of snoring sounds of the subject (e.g., while the subject is sleeping). In some embodiments, detection component 63 may be configured to detect OSA event(s) (and/or inspiratory flow limited occurrences) while the subject is awake. For example, by measuring compensatory muscular activation of the upper airway (the muscles of the neck, tongue and/or throat) during wakefulness. This muscular activation appears to be particularly prevalent in the genioglossus (GG) muscle, which is a muscle of the human body that runs from the chin to the tongue. The GG muscle is the major muscle responsible for protruding (or sticking out) the tongue. This increased compensatory muscular activation appears to be a product of an increased tonic activation of the muscle, combined with increased negative-pressure generation during inspiration. In some embodiments, detection component 63 may be configured to measure the subject's compliance in the presence and absence of a magnetic stimulation of the upper airway muscles. Magnetic stimulation is used to stimulate muscles which serve to stabilize the upper airway of an individual whose nocturnal apneic event(s) are related to diminished muscle tone. Sensor(s) 40 monitors a physiologic characteristic of the subject, a coil is energized to stimulate the appropriate muscles associated with the upper airway, a power supply provides power for energizing the coil, and a control system controls the application of power to the coil based on the output of sensor(s) 40.

In other embodiments, a tremor resulting from increased muscle (e.g., GG muscle) activation is measured during wakefulness using acoustic pharyngometry in order to identify the characteristic modulation (e.g., 30-40 Hz or some other frequency range or ranges) associated with OSA event(s) to determine whether the subject is experiencing an OSA event. As is known in the art, acoustic pharyngometry is a dynamic test that determines dimensions of the oral airway past the glottis while the subject is breathing. In particular, acoustic pharyngometry uses an acoustic reflection technique to measure the cross-sectional area of at least a portion of the subject's upper airway during inspiration.

In some embodiments, detection component 63 may be configured to detect collapse of the lower airways during exhalation. Collapse of the lower airways during exhalation may be and/or cause expiratory flow limitation (EFL), a condition when an increase in transpulmonary pressure causes no corresponding increase in expiratory flow due to "choke points" in the many bronchial branches which is the hallmark of COPD. COPD is a progressive and irreversible disease that affects the lung function but also has significant extra-pulmonary effects. The more severe COPD subjects have frequent acute exacerbations (AE-COPD: a sudden worsening of the symptoms) that these may require hospitalization. A better management of subjects at home, including prediction of acute exacerbations with sufficient lead time, may reduce hospitalizations, morbidity, mortality, and improve quality of life. Collapse of the lower airways during exhalation may cause pulmonary gases, including $CO_2$, to be trapped in the alveolar region of the lungs which causes poor gas exchange and a buildup of $CO_2$ in the blood. In addition to EFL, COPD may be detected using cough monitoring, blood oxygenation measurement, questionnaires, and/or other techniques.

In some embodiments, EFL may be detected based on the output signals, parameters determined by parameter component 62, and/or other information. For example, EFL may be detected based on output signals from a pulse oximeter (e.g., included in sensor(s) 40), an electromyogram, a pressure sensor, a flow sensor, forced oscillation technique, and/or other detection techniques. In some embodiments, Forced Oscillation Technique (FOT) may be used to detect EFL. As explained above, FOT works by comparing the phase shift of the small amplitude oscillations on the flow signal to the oscillations on the pressure signal. When there is a pulmonary obstruction or change in the inertial properties of the lung there is an offset in the arrival time between these two signals. Airway impedance can be deduced by the mechanical response to these small time varying changes. The impedance can mathematically be further broken down into two components, resistance and reactance. The expiratory reactance component has been shown to correlate to a subject's degree of Expiratory Flow Limitation (EFL).

Therapy determination component 64, may be configured to determine one or more therapy parameters for treating one or more respiratory disorders in response to detecting a respiratory disorder. In some embodiments, the therapy determination component 64 may be configured to determine therapy parameters for one or more disorders in response to a request from a user and/or from one or more components of system 100. The one or more therapy parameters may include pressure, flow, volume, and/or other parameters. For example, in some embodiments, responsive to detecting presence of an OSA event(s), determination component 64, may be configured to determine one or more therapy parameters for treating OSA event(s) (and/or inspiratory flow limited occurrences). In some embodiments, in response to detecting EFL, determination component 64, is configured to determine one or more EFL therapy parameters for treating the detected EFL in the subject. In some embodiments, the one or more therapy parameters for OSA event(s) may comprise pressure for treating OSA (POSA) event(s), and the one or more therapy parameters for EFL comprise pressure for treating EFL(PEFL). In some embodiments, therapy determination component 64 may be configured to lowering AHI (apnea hypopnea index (# of apneas and hypopneas/1 hour). For example by capturing the OSA event(s), calculate an AHI, and then change the pressure of the ventilator to lower the "running AHI" score.

In some embodiments, comparison component 66 is configured to compare one or more therapy parameters for one or more diseases (e.g., between OSA event(s) therapy parameters and EFL therapy parameters, and/or other diseases). For example, comparison component 66 may be configured to compare POSA and PEFL. In some embodiments, comparison component 66 may be configured to compare other therapy parameters. In some embodiments, comparison component 66 may be configured to compare other parameters received from other components within or outside system 100. In some embodiments, the comparison step may be performed with other components of system 100 (e.g., priority component 68 described below, therapy determination component, or other components).

Priority component 68 is configured to determine a priority treatment for one or more diseases. In some embodiments, determination of the priority treatment is based on a comparison by comparison component 66. In some embodiments, priority component 68 may be configured to determine a preference of the airway pressure delivered to the subject based on the value of either the inspiratory phase of the real component of the impedance (indicative of their airway resistance), or the value of the expiratory phase of the imaginary, i.e. reactance component of the subject's airway impedance (indicative of their expiratory flow limitation). In some embodiments, a subject's airway collapse, or upper airway obstruction may be determined by an increase in airway inspiratory resistance, and a subject's expiratory flow limitation may be determined by a decrease (negatively) value of their expiratory reactance. In some embodiments, priority component 68 may be configured to prioritize the pressure required to treat the subject's upper airway obstruction over the pressure required to treat the subject's expiratory flow limitation and for the ventilator to adjust its pressure settings accordingly. This would give priority to treating upper airway obstruction over lower airway expiratory flow limitation. This logic may be advantageous because it is clinically more important to treat a subject's OSA event(s) due to its profound medical implications (e.g., increased risk of heart failure and generally, subjects with untreated OSA event(s) have a substantially greater risk of morbidity and mortality). The patency of the upper airway or the reduction or elimination of inspiratory flow limitation occurrence may be a better priority because if OSA event(s) is not managed, then it becomes increasing to nearly impossible to manage expiratory flow limitation. In addition, at the therapeutic pressure levels required to treat a subject's OSA event(s), that it is likely that the majority of subjects will have their EFL benefited as well.

The following table, illustrates an example of therapy determination based on detection of EFL (associated with COPD) and/or OSA events:

| EFL | OSA EVENTS | Pressure effect |
| --- | --- | --- |
| Present | Present | Increase pressure |
| Present | Neutral/unknown | Increase pressure |
| Negative (not present) | Present | Increase pressure |
| Negative (not present) | Negative (not present) | Decrease pressure |
| Neutral/unknown | Present | Increase pressure |
| Neutral/unknown | Negative | Decrease pressure |

For example, priority component 68 may make a determination to increase pressure of the breathable gas delivered to the subject responsive to detecting presence of EFL (regardless of presence of OSA event(s)); presence of OSA event(s) (regardless of presence of EFL), or presence of EFL and OSA event(s) concurrently. The priority component 68 may make a determination to decrease pressure of the breathable gas delivered to the subject responsive to not detecting EFL, and/or OSA event(s).

In some embodiments, priority component 68 may give priority to the higher of the two pressures. However, this may have the consequence of potentially hyper-inflating the subject if their obstructive pressure required to obliterate their obstruction is greater than the pressure required to reduce or eliminate their expiratory flow limitation or else under treating their obstructive disorder if the expiratory pressure is deemed to be higher. In some embodiments, if the ventilator determines that the pressure required to resolve a subject's EFL is higher than the determined pressure to treat a subject's OSA event, then the pressure delivered by the ventilator will be offset positively by 0.1 cmH$_2$O, or 0.2 cmH$_2$O, or 0.3 cmH$_2$O, etc. up to 2 cmH$_2$O above the determined OSA event pressure based on a proprietary set of COPD-OSA overlap rules within the ventilator that considers the differential between the two determined pressures, as well as, the percent of breaths that are expiratory flow limited, and sets the pressure accordingly.

Control component 69 may be configured to control pressure generator 20 to generate the flow of gas in accordance with one or more therapy regimes. In some embodiments, control component 69 may be configured to control pressure generator 20 to deliver the priority treatment determined by priority component 68. Control component 69 may be configured to control pressure generator 20 based on the output signals from sensor(s) 40, information from parameter component 62, comparison by comparison component 66, priority determined by priority component 68, and/or based on other information. In some embodiments, control component 69 may be configured to control pressure generator 20 based on information (or input) for a user.

Figure 3:
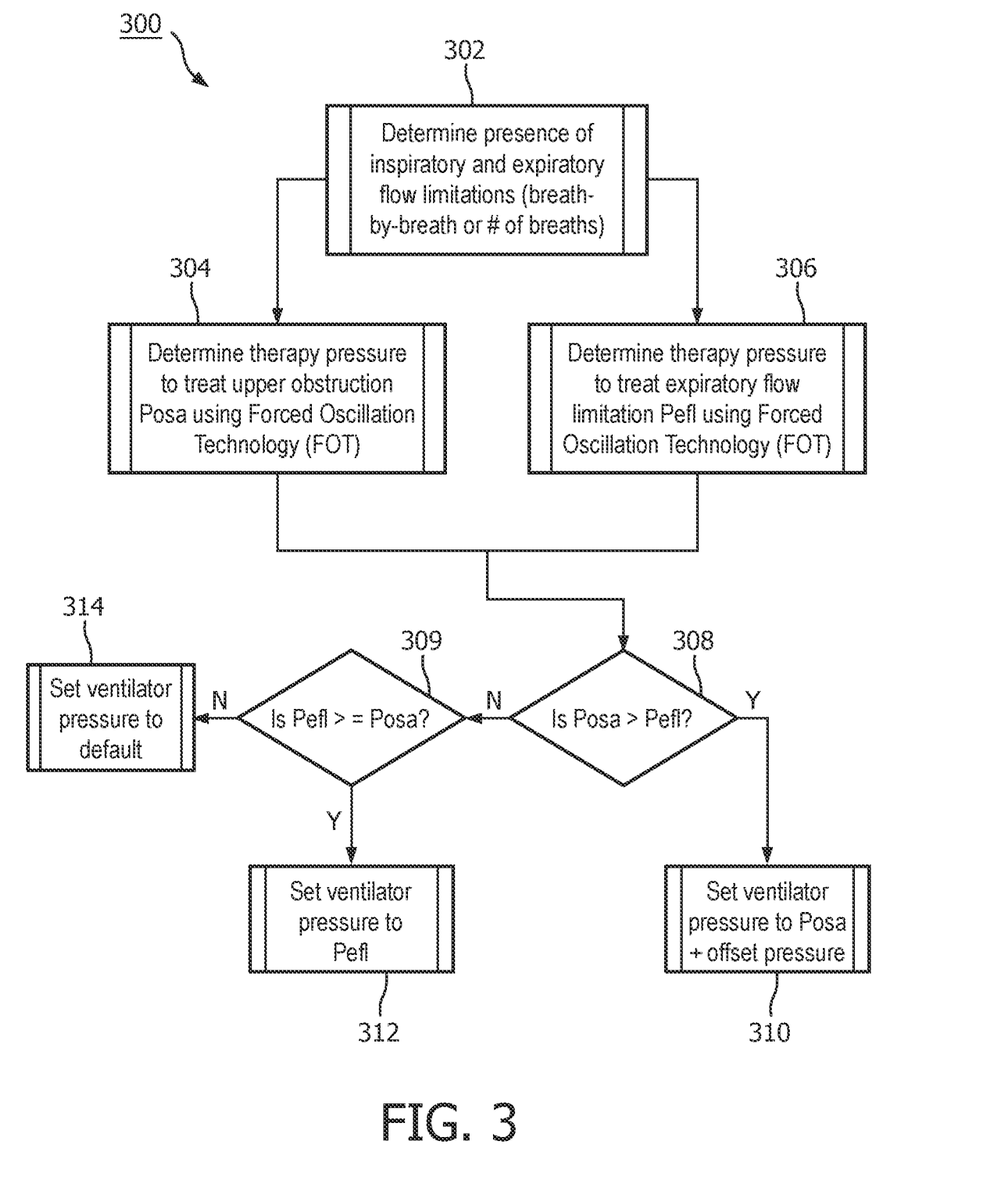
FIG. 3 illustrates an example of an algorithm for treatment delivered by system 100, according to one or more embodiments.

FIG. 3 illustrates an example 300 of an algorithm for treatment delivered by system 100. In this example, detection component 63 (described above and not shown here) may determine presence of inspiratory and expiratory flow limitations occurrence (e.g., breath by breath or number of breaths) 302. Responsive to determination 302, therapy determination component 64 (described above and not shown here) may determine therapy parameters 304 to treat upper obstruction, and therapy parameters 306 to treat expiration flow limitation. In some embodiments, therapy parameters 304, and/or 306 may be determined using forced oscillation technique (FOT). In some embodiments, as explained above, other techniques for determining therapy parameters may be used. In some embodiments, therapy parameters 304 may include pressure to treat OSA event(s) (POSA), and therapy parameters 306 may include pressure to treat EFL connected to COPD (PEFL).

In some embodiments, responsive to one or more therapy parameters 304 being greater than one or more therapy parameters 306 (e.g., POSA>PEFL) 308, the control component 69 (described above and not shown here) is configured to set the ventilator pressure to POSA+an offset pressure 310. For example, offset positively by 0.1 cmH$_2$O, or 0.2 cmH$_2$O, or 0.3 cmH$_2$O, etc. up to 2 cmH$_2$O above the determined POSA. Responsive to one or more therapy parameters 306 being greater or equal to one or more therapy parameters 304 (e.g., PEFL>POSA) 309, the control component 69 is configured to set the ventilator pressure to PEFL 312. Responsive to one or more therapy parameters 304 not being greater than one or more therapy parameters 306, and one or more therapy parameters 306 not being greater or equal to one or more therapy parameters 304, the control component 69 may be configured to set the ventilator pressure to a default pressure 314 (e.g., default pressure may be set by the user).

User interface 120 is configured to provide an interface between system 100 and subject 70 and/or other users through which subject 70 and/or other users may provide information to and receive information from system 100. Other users may comprise, for example, a caregiver, a doctor, and/or other users. This enables data, cues, results, and/or instructions and any other communicable items, collectively referred to as "information," to be communicated between a user (e.g., subject 70) and one or more of pressure generator 20, Processor(s) 60, and/or other components of system 100. For example, a user may specify one or more therapy regimes and one or more therapy set points that are to be delivered to subject 70 using user interface 120. For example, a user may define therapy set points including a base expiratory pressure level and a base inspiratory pressure level of a positive pressure support therapy using interface 120. Control component 69 may then customize the therapy regime delivered to the subject based on the one or more inputs made by the user to the user interface. As another example, therapy pressures, the breath rate of subject 70, and/or other information may be displayed to a user (e.g., subject 70) via user interface 120. Examples of interface devices suitable for inclusion in user interface 120 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 120 comprises a plurality of separate interfaces.

It is to be understood that other communication techniques, either hard-wired or wireless, are also contemplated by the present disclosure as user interface 120. For example, the present disclosure contemplates that user interface 120 may be integrated with a removable storage interface provided by electronic storage 130. In this example, information may be loaded into system 100 from removable storage (e.g., a smart card, a flash drive, a removable disk, etc.) that enables the user(s) to customize the implementation of system 100. Other exemplary input devices and techniques adapted for use with system 100 as user interface 120 comprise, but are not limited to, an RS-232 port, RF link, an IR link, modem (telephone, cable or other). In short, any technique for communicating information with system 100 is contemplated by the present disclosure as user interface 120.

In some embodiments, electronic storage 130 comprises electronic storage media that electronically stores information. The electronic storage media of electronic storage 130 may comprise one or both of system storage that is provided integrally (i.e., substantially non-removable) with system 100 and/or removable storage that is removably connectable to system 100 via, for example, a port (e.g., a USB port, a firewire port, etc.) or a drive (e.g., a disk drive, etc.). Electronic storage 130 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 may store software algorithms, information determined by Processor(s) 60, information received via user interface 120, and/or other information that enables system 100 to function properly. Electronic storage 130 may be (in whole or in part) a separate component within system 100, or electronic storage 130 may be provided (in whole or in part) integrally with one or more other components of system 100 (e.g., user interface 120, Processor(s) 60, etc.).

Information determined by Processor(s) 60 and/or stored by electronic storage 130 may comprise information related to respiration of subject 70, compliance, use frequency, and/or other information. The information stored by electronic storage 130 may be viewed via user interface 120, by connecting (wired and/or wireless) to a separate computer, and/or other via other methods. The information stored by electronic storage 130 may be used, for example, to adjust therapy settings, used by a doctor to make medical decisions, and/or for other uses. In some embodiments, system 100 may include a wireless transmitter (not shown) and the information determined by Processor(s) 60, the information stored by electronic storage 130, and/or other information may be communicated to a care giver, for example, over a wireless network. By way of a non-limiting example, the care giver may receive use information, subject status, and/or other information, allowing the care giver to remotely track the therapy delivered by system 100.

Figure 4:
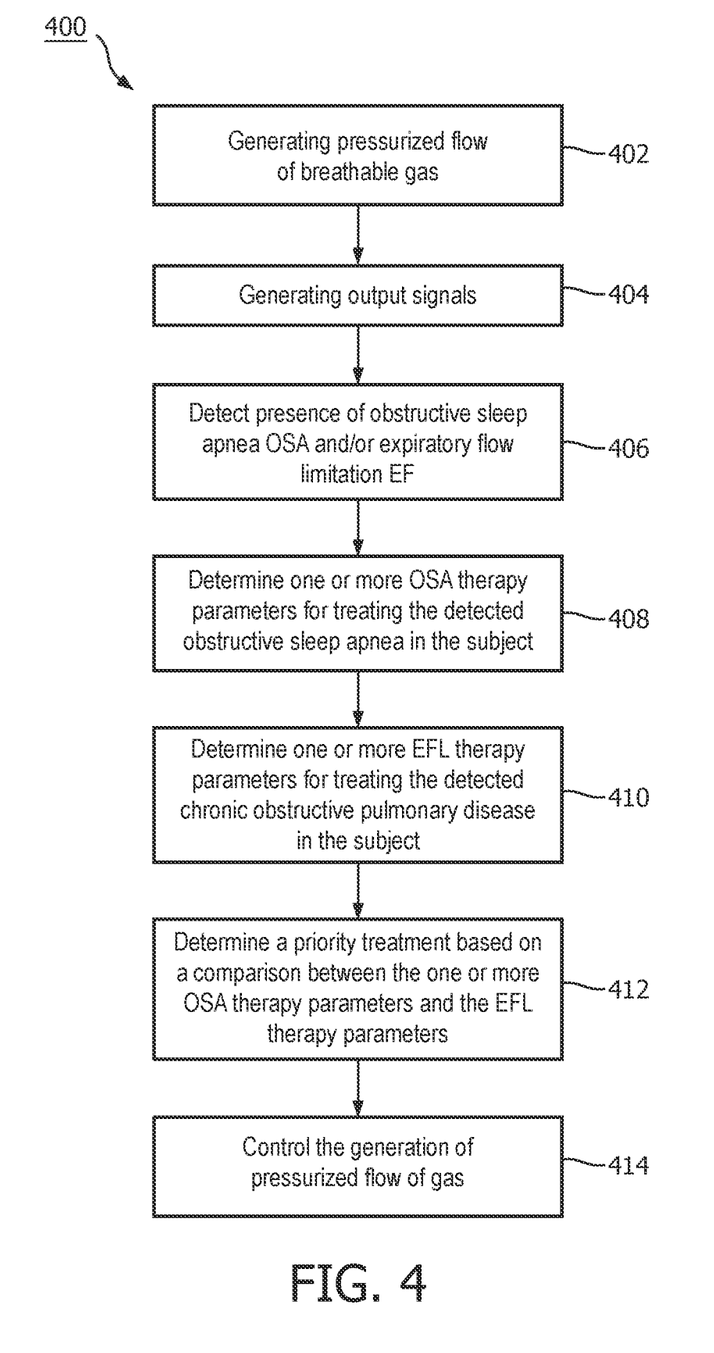
FIG. 4 illustrates a method for detecting and treating COPD-OSA overlap syndrome, according to one or more embodiments.

FIG. 4 illustrates a method 400 for detecting and treating concurrent chronic obstructive pulmonary disease (COPD) and obstructive sleep apnea event(s)(OSA) overlap syndrome with a ventilator system. The respiratory system comprises a pressure generator, one or more sensors, one or more physical computer processors, and/or other components. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, a pressurized flow of breathable gas for delivery to the airway of the subject is generated. In some embodiments, the pressurized flow of breathable gas is generated by a pressure generator similar to and/or the same as pressure generator 20 (shown in FIGS. 1 and 2, and described herein).

At an operation 404, output signals conveying information related to one or more parameters of the breathable gas are generated. In some embodiments, operation 404 is performed by one or more sensors the same as or similar to sensor(s) 40 (shown in FIGS. 1 and 2, and described herein).

At an operation 406, presence of obstructive sleep apnea OSA event(s) and/or expiratory flow limitation EFL is detected. In some embodiments, operation 406 is performed by a physical computer processor the same as or similar to Processor(s) 60 (shown in FIGS. 1 and 2, and described herein).

At an operation 408, one or more OSA event(s) therapy parameters for treating the detected obstructive sleep apnea event(s)(and/or inspiratory flow limited occurrences) in the subject is determined. In some embodiments, operation 408 is performed by a physical computer processor the same as or similar to Processor(s) 60 (shown in FIGS. 1 and 2, and described herein).

At an operation 410, one or more EFL therapy parameters for treating the detected EFL in the subject is determined. In some embodiments, operation 410 is performed by a physical computer processor the same as or similar to Processor(s) 60 (shown in FIGS. 1 and 2, and described herein).

At an operation 412, a priority treatment to be delivered to the subject is determined. In some embodiments, the priority treatment is determined based on a comparison between the one or more OSA event(s) therapy parameters and the EFL therapy parameters. In some embodiments, operation 412 is performed by a physical computer processor the same as or similar to Processor(s) 60 (shown in FIGS. 1 and 2, and described herein).

At an operation 414, the generation of pressurized flow of breathable gas is controlled to deliver the priority treatment. In some embodiments operation 408 is performed by a physical computer processor the same as or similar to Processor(s) 60 (shown in FIGS. 1 and 2, and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A ventilator system for detecting and treating concurrent chronic obstructive pulmonary disease (COPD) and obstructive sleep apnea (OSA) event(s) overlap syndrome, the ventilator system comprising:
   a pressure generator configured to generate a pressurized flow of breathable gas for delivery to an airway of a subject;
   one or more sensors configured to generate output signals conveying information related to one or more parameters related to the breathable gas; and
   one or more physical computer processors operatively connected to the one or more sensors and the pressure generator, the one or more physical computer processors configured by computer readable instructions to:
      detect presence of obstructive sleep apnea OSA event(s) and/or expiratory flow limitation (EFL) in the subject based on the output signals; and
      responsive to detecting concurrent presence of the OSA event(s) and the EFL:
         determine one or more OSA event(s) therapy parameters indicative of one or more of a first pressure, a first flow, and a first volume for treating the detected obstructive sleep apnea in the subject;

determine one or more EFL therapy parameters indicative of one or more of a second pressure, a second flow, and a second volume for treating the detected expiratory flow limitation in the subject;

determine a priority treatment based on a comparison between the one or more OSA event(s) therapy parameters and the one or more EFL therapy parameters; and control the pressure generator to deliver the determined priority treatment to the subject.

2. The ventilator system of claim 1, wherein detecting presence of OSA event(s) in the subject comprises detecting upper airway obstruction in the subject based on the output signals.

3. The ventilator system of claim 1, wherein the one or more physical computer processors are further configured to:

responsive to a first OSA event therapy parameter being greater than a corresponding first EFL therapy parameter, control the ventilator system to deliver a cumulative first parameter, the cumulative first parameter being a cumulative of the first OSA event therapy parameter and a first parameter offset; and responsive to the first EFL therapy parameter being greater than or equal to the first OSA event therapy parameter, control the ventilator system to deliver the first EFL therapy parameter.

4. The ventilator system of claim 1, wherein the one or more OSA event(s) therapy parameters comprise the first pressure for treating OSA event(s) (POSA).

5. The ventilator system of claim 1, wherein the one or more EFL therapy parameters comprise the second pressure for treating EFL (PEFL).

6. The ventilator system of claim 1, wherein the one or more physical computer processors are further configured to: deliver a forced oscillation technique (FOT) to determine the one or more OSA event(s) therapy parameters and/or the one or more EFL therapy parameters.

7. The ventilator system of claim 1, wherein the one or more physical computer processors are further configured to: prioritize treatment of the detected OSA event(s) over treatment for the detected EFL.

8. The ventilator system of claim 1, wherein detecting presence of the OSA event(s) in the subject comprises detecting upper airway obstruction in the subject based on an apnea and hypopnea index AHI).

9. A method for detecting and treating concurrent chronic obstructive pulmonary disease (COPD) and obstructive sleep apnea (OSA) event overlap syndrome with a ventilator system comprising a pressure generator, one or more sensors, and one or more physical computer processors, the method comprising:

generating a pressurized flow of breathable gas for delivery to an airway of a subject with the pressure generator;

generating output signals conveying information related to one or more parameters of the breathable gas with the one or more sensors;

detecting, with the one or more physical computer processors presence of obstructive sleep apnea OSA event(s) and/or expiratory flow limitation (EFL) in the subject based on the output signals;

responsive to detecting concurrent presence of the OSA event(s) and the EFL:

determining, with the one or more physical computer processors, one or more OSA event(s) therapy parameters indicative of one or more of a first pressure, a first flow, and a first volume for treating the detected obstructive sleep apnea in the subject;

determining, with the one or more physical computer processors, one or more EFL therapy parameters indicative of one or more of a second pressure, a second flow, and a second volume for treating the detected expiratory flow limitation in the subject;

determining, with the one or more physical computer processors, a priority treatment based on a comparison between the one or more OSA event(s) therapy parameters and the one or more EFL therapy parameters; and controlling, with the one or more physical computer processors, the pressure generator to deliver the determined priority treatment to the subject.

10. The method of claim 9, wherein detecting the presence of OSA event(s) in the subject comprises detecting upper airway obstruction in the subject based on the output signals.

11. The method of claim 9, further comprising:

responsive to a first OSA event(s) therapy parameter being greater than a corresponding first EFL therapy parameter, controlling the ventilator system to deliver a cumulative first parameter, the cumulative first parameter being a cumulative of the first OSA event(s) therapy parameter and a first parameter offset; and responsive to the first EFL therapy parameter being greater than or equal to the first OSA event(s) therapy parameter, controlling the ventilator system to deliver the first EFL therapy parameter.

12. The method of claim 9, wherein the one or more OSA event(s) therapy parameters comprise the first pressure for treating OSA event(s) (POSA).

13. The method of claim 9, wherein the one or more EFL therapy parameters comprise the second pressure for treating EFL (PEFL).

14. The method of claim 9, further comprising: delivering a forced oscillation technique (FOT) to determine the one or more OSA event(s) therapy parameters and/or the one or more EFL therapy parameters.

15. The method of claim 9, further comprising: prioritizing treatment of the detected OSA event(s) over treatment for the detected EFL.

16. The method of claim 9, wherein detecting presence of OSA event(s) in the subject comprises detecting upper airway obstruction in the subject based on an apnea and hypopnea index (AHI).

17. A ventilator system for detecting and treating concurrent chronic obstructive pulmonary disease (COPD) and obstructive sleep apnea (OSA) event(s) overlap syndrome, the ventilator system comprising:

means for generating a pressurized flow of breathable gas for delivery to the airway of a subject;

means for generating output signals conveying information related to one or more parameters of the breathable gas;

means for detecting, with the one or more physical computer processors presence of obstructive sleep apnea OSA event(s) and/or expiratory flow limitation (EFL) in the subject based on the output signals; and means for, responsive to detecting concurrent presence of the OSA event(s) and the EFL:

determining one or more OSA event(s) therapy parameters indicative of one or more of a first pressure, a first flow, and a first volume for treating the detected obstructive sleep apnea in the subject;

determining one or more EFL therapy parameters indicative of one or more of a second pressure, a second flow, and a second volume for treating the detected expiratory flow limitation in the subject;

determining a priority treatment based on a comparison between the one or more OSA event(s) therapy parameters and the one or more EFL therapy parameters; and controlling the pressure generator to deliver the determined priority treatment to the subject.

18. The system of claim 17, wherein detecting presence of OSA event(s) in the subject comprises detecting upper airway obstruction in the subject based on the output signals.

19. The system of claim 17, further comprising:

means for:

responsive to a first OSA event therapy parameter being greater than a corresponding first EFL therapy parameter, controlling the ventilator to deliver a cumulative first parameter, the cumulative first parameter being a cumulative of the first OSA event(s) therapy parameter and a first parameter offset; and responsive to the first EFL therapy parameter being greater than or equal to the first OSA event(s) therapy parameter, controlling the ventilator to deliver the first EFL therapy parameter.

20. The system of claim 17, wherein the one or more OSA event(s) therapy parameters comprise the first pressure for treating OSA event(s) (POSA).

21. The system of claim 17, wherein the one or more EFL therapy parameters comprise the second pressure for treating EFL (PEFL).

22. The system of claim 17, further comprising: means for delivering a forced oscillation technique (FOT) to determine the one or more OSA event(s) therapy parameters and/or the one or more EFL therapy parameters.

23. The system of claim 17, further comprising: means for prioritizing treatment of the detected OSA event(s) over treatment for the detected EFL.

24. The system of claim 17, wherein detecting presence of OSA event(s) in the subject comprises detecting upper airway obstruction in the subject based on an apnea and hypopnea index AHI.

* * * * *